United States Patent [19]

Imokawa et al.

[11] Patent Number: 5,610,408
[45] Date of Patent: Mar. 11, 1997

[54] PROCESS FOR PREPARING LIQUID DIPHENYLMETHANE DIISOCYANATE

[75] Inventors: Toshiaki Imokawa, Niihama; Yoshiharu Kato, Ehime-ken, both of Japan

[73] Assignee: Sumitoma Bayer Urethane Co., Ltd., Amagasaki, Japan

[21] Appl. No.: 520,545

[22] Filed: Aug. 28, 1995

[30] Foreign Application Priority Data

Aug. 30, 1994 [JP] Japan .................................. 6-243516

[51] Int. Cl.⁶ ............................................... C09K 3/00
[52] U.S. Cl. ........................................ 252/182.2; 560/334
[58] Field of Search ........................... 560/331, 333, 560/334; 568/12, 8; 252/182.2

[56] References Cited

U.S. PATENT DOCUMENTS

| | | | |
|---|---|---|---|
| 2,663,736 | 8/1951 | McCormack | 562/812 |
| 2,663,737 | 8/1951 | McCormack | 568/12 |
| 2,663,739 | 8/1951 | McCormack | 568/12 |
| 3,384,653 | 5/1968 | Erner et al. | 560/333 |
| 3,449,256 | 6/1969 | Farrissey, Jr. | 252/182 |
| 4,088,665 | 5/1978 | Findeisen et al. | 560/334 |
| 4,120,884 | 10/1978 | Woerner et al. | 560/331 |
| 4,154,752 | 5/1979 | Sundermann et al. | 260/453 SP |
| 5,202,358 | 4/1993 | Scholl et al. | 521/160 |
| 5,258,548 | 11/1993 | Imokawa | 560/333 |

FOREIGN PATENT DOCUMENTS

| | | |
|---|---|---|
| 531803 | 3/1993 | European Pat. Off. . |
| 48-22694 | 7/1973 | Japan . |
| 52-100600 | 8/1977 | Japan . |
| 62-190213 | 8/1987 | Japan . |
| 93/23367 | 11/1993 | WIPO . |

*Primary Examiner*—Charles T. Jordan
*Assistant Examiner*—John R. Hardee
*Attorney, Agent, or Firm*—Joseph C. Gil

[57] ABSTRACT

A process for preparing a liquid MDI, which comprises adding, to MDI, a phospholine catalyst and a phosphorous acid ester of a specified formula and conducting a carbodiimidization reaction.

1 Claim, No Drawings

PROCESS FOR PREPARING LIQUID DIPHENYLMETHANE DIISOCYANATE

BACKGROUND OF THE INVENTION

The present invention relates to a liquefaction of diphenylmethane diisocyanate (hereinafter referred to as "MDI") and a process for preparing liquid MDI.

MDI has a very high reactivity and is a very useful compound as a raw material for polyurethane resin prepared by the reaction with a polyol mixture containing an active hydrogen compound, and an additive such as a chain extender and a catalyst.

Polyurethanes prepared from MDI are widely used as molded articles such as bumpers of automobile, foams such as seat cushions, cast elastomers, sealing materials and the like.

MDI usually comprises the 4,4'-isomer together with a small amount of the 2,4'-isomer. Both isomers are solid at room temperature and their melting points are 42° C. and 36° C., respectively. MDI often contains small amounts of the 2,2'-isomer. In any event, MDI, which is a mixture containing 4,4'-isomer, is solid at room temperature.

When MDI is used for a raw material for polyurethane, it is advantageous that MDI be liquid, in view of the storing and handling of the raw material. For this purpose, there is a method for preparing liquid MDI in which a catalyst is added to MDI to conduct a reaction (Japanese Patent Kokoku Publication No. 7545/1970, corresponding to U.S. Pat. No. 3,384,653). However, this method is not always a sufficient method for preparing liquid MDI, since MDI considerably discolors because of a relatively large amount of catalyst and a high reaction temperature and the removal of a solid by-product is necessary.

Japanese Patent Kokai Publication No. 100600/1977 (corresponding to U.S. Pat. No. 4,120,884) discloses a method for preparing liquid having a good storage stability, which comprises adding a phospholine catalyst to MDI to produce a carbodiimide. This method is preferable, since the amount of the added catalyst is small, e.g., several ppm to several dozen ppm. The phospholine catalyst has a very high activity so that the amount of the added catalyst is very small, but an impurity such as an acid or hydrolyzable chlorine, which is contained in a very small amount in MDI, gives a strong effect on MDI and the same amounts of the added catalyst do not necessarily give liquid MDI having stable properties.

The above problems become even more pronounced when the composition of the isomers of MDI used for liquefaction is varied and the change of content of the small amount impurity increases. In some cases, the addition of catalyst can give no carbodiimidization so that MDI having the desired properties cannot be obtained.

DESCRIPTION OF THE INVENTION

It has now been found that when certain phosphorous acid esters are used together with a phospholine catalyst, the resultant liquid MDI has stable properties and good storage stability.

The present invention relates to a process for preparing a liquid MDI, which comprises adding, to MDI, a phospholine catalyst and a phosphorous acid ester of the formula (I):

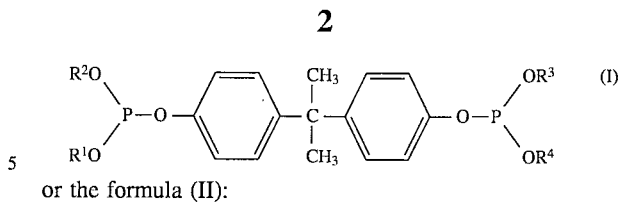

or the formula (II):

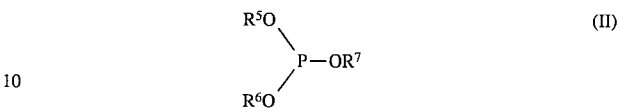

wherein $R^1$, $R^2$, $R^3$, $R^4$, $R^5$, $R^6$ and $R^7$ can be the same or different and each represents a $C_{20}$ alkyl group, stirring the mixture at a temperature of from 60° to 80° C. for a period of from 1 to 10 hours, adding a deactivating agent to the mixture once the desired degree of carbodiimidization has been reached.

MDI is a solid compound at a room temperature which comprises a large amount of 4,4'-isomer, a small amount of 2,4'-isomer and in some cases, very small amounts of the 2,2'-isomer. MDI is also pure MDI or purified MDI.

Specific examples of the phospholine compound which is the catalyst are phospholines, phospholidines, oxides, phospholidine oxides and derivatives thereof, as described in the above Japanese Kokai Publication No.1006000/1977. 1-Phenyl-3-methylphospholine and 1-ethyl-3-methylphospholidine-1-oxide are preferred and 1-methylphospholine-1-oxide is particularly preferred.

The amount of the catalyst is varied based upon on the composition of MDI and is usually from 0.0001 to 0.005 parts by weight, preferably from 0.0002 to 0.002 parts by weight, per 100 parts by weight of MDI.

The phosphorous acid ester of the above formula (I) or (II) is preferably tetratridecyl-4,4'-isopropylidenediphenyldiphosphite (hereinafter referred to as tridecyl compound), tributyl phosphite, tri(2-ethylhexyl) phosphite, tridecyl phosphite and tristearyl phosphite.

The phosphorous acid ester is used as an anti-discoloring agent and a stabilizer (cf. Japanese Patent Kokai Publication No. 65264/1993, corresponding to U.S. Pat. No. 5,258,548). Liquid MDI containing the phosphorous acid ester can be stably stored for a long time.

The amount of the phosphorous acid ester is varied depending on the composition of MDI as in the case of the catalyst and is usually from 0.001 to 0.1 parts by weight, preferably from 0.005 to 0.05 parts by weight, per 100 parts by weight of MDI. Generally, the amount of the phosphorous acid ester is several dozen times to several hundred times the amount of the catalyst.

Liquid MDI according to the present invention can be prepared by heating MDI which is solid at room temperature, to 40°–60° C. to liquefy MDI; adding the above catalyst and phosphorous acid ester in the given amounts; stirring the mixture at 60°–80° C. for 1–10 hours, preferably for 3–6 hours: adding a deactivating agent, for example, butyl carbamic acid chloride or acetyl chloride to discontinue the reaction, when a carbodiimidation degree reaches a desired degree.

The carbodiimidation degree can be monitored by measuring the NCO content of the liquid MDI. In order to obtain liquid MDI having the stable properties, the NCO content is preferably from 29 to 31.5%.

The invention is further illustrated but is not intended to be limited by the following examples in which all parts and percentages are by weight unless otherwise specified.

EXAMPLES

Example 1 and Comparative Example 1

Purified MDI (melting point: 38.7° C.) was liquefied by heating MDI to 40°–50° C. 1-Methylphospholine-1oxide (3 ppm) was added, then tridecyl compound (500 ppm) was added and the mixture was stirred at 70° C. for 6 hours. In comparison, the mixture without the addition of the tridecyl compound was stirred.

The mixture was sampled and the NCO content (in %) was measured. After butyl carbamic acid chloride (3 ppm) was added to discontinue the reaction, the mixture was cooled to room temperature and was stored for one week.

When the tridecyl compound was added, MDI kept the liquid state. When the tridecyl compound was not added, MDI was opaque after one day and was fully solid after one week.

The NCO content was 30.4% in the case of the addition of the tridecyl compound and 32.8% in the case of no addition of the tridecyl compound.

Example 2

Purified MDI (melting point: 38.8° C.) was liquefied by heating MDI to 40°–50° C. 1-Methylphospholine-1-oxide (3 ppm) was added and the mixture was stirred at 70° C. for 3 hours. The mixture was sampled and the NCO content was measured to be 33.5%.

Then the tridecyl compound (500 ppm) was added and the mixture was stirred at 70° C. for 5 hours. The mixture was sampled and the NCO content was measured to be 30%. Butyl carbamic acid chloride (3 ppm) was added to discontinue the reaction.

Then the mixture was stored at room temperature for one week. The MDI kept the liquid state.

Examples 3–7 and Comparative Examples 2–4

In the same manner as in Example 1,200 ppm of the phosphorous acid ester showing in Tables 1 and 2 was added to prepare liquid MDI. The NCO content (in %) was measured. The results are shown in Tables 1 and 2.

In comparison, Tables 2 and 3 show the results of no addition of the phosphorous acid ester and the addition of the phosphorous acid ester other than those of the present invention.

TABLE 1

|  | Example 3 | Example 4 | Example 5 |
|---|---|---|---|
| additive | Tridecyl compound | Tributyl phosphite | Tri(2-ethylhexyl) phosphite |
| hours for heating and stirring | 6 | 3.1 | 2.8 |
| NCO content (%) | 31.2 | 30 | 30 |

TABLE 2

|  | Example 6 | Example 7 | Comparative Example 2 |
|---|---|---|---|
| additive | Tridecyl phosphite | Tristearyl phosphite | not added |
| hours for heating and stirring | 3.9 | 6 | 6 |
| NCO content (%) | 30 | 31.4 | 32.8 |

TABLE 3

|  | Comparative Example 3 | Comparative Example 4 | Comparative Example 5 |
|---|---|---|---|
| additive | Trinonylphenyl phosphite | Tetraphenyl-dipropylene-glycol-diphosphate | Triphenyl phosphite |
| hours for heating and stirring | 6 | 6 | 6 |
| NCO content (%) | 32.8 | 32.7 | 33 |

Example 8

Two purified MDI's having the different isomer compositions and impurity contents shown in Tables 4 and 5 were used. A phosphorous acid ester was added or was not added in the presence of a catalyst to attempt to liquefy MDI in the same manner as in Example 1 or Comparative Example 1. The results of the state after storage for 10 days are shown in Tables 4 and 5.

TABLE 4

|  | Purified MDI-A |
|---|---|
| Melting point (°C.) | 38.7 |
| 2,4'-isomer (%) | 1.09 |
| 4,4'-isomer (%) | 98.9 |
| 2,2'-isomer (%) | 0.01 |
| Acid content (ppm) | 3 |
| Hydrolyzable chlorine (ppm) | 7 |

|  | Example 8-1 | Comparative Example 8-1 |
|---|---|---|
| Tridecyl compound (ppm) | 200 | 0 |
| 1-Methylphospholine 1-oxide (ppm) | 3 | 3 |
| Hours for heating and stirring | 6 | 6 |
| Liquid MDI | O | X |
| Viscosity (cps) | 26 | — |
| NCO content (%) | 31.3 | 33.2 |
| Hue (APHA) | 30 | — |

TABLE 5

|  | Purified MDI-B |
|---|---|
| Melting point (°C.) | 38.2 |
| 2,4'-isomer (%) | 1.69 |
| 4,4'-isomer (%) | 98.31 |
| 2,2'-isomer (%) | trace |
| Acid content (ppm) | 6 |
| Hydrolyzable chlorine (ppm) | 10 |

|  | Examples 8-2 | Comparative Examples 8-2 |
|---|---|---|
| Tridecyl compound (ppm) | 200 | 0 |
| 1-Methylphospholine 1-oxide (ppm) | 3 | 3 |
| Hours for heating and stirring | 5.4 | 6 |
| Liquid MDI | O | X |
| Viscosity (cps) | 28 | — |
| NCO content (%) | 30.3 | 32.3 |
| Hue (APHA) | 40 | — |

Note:
O: The liquid states were kept after 10 days.
X: The solid states were made after 10 days.

The process according to the present invention can produce liquid MDI having stable properties. This liquid MDI has almost no discoloring, even if it is stored for a long time. The present process can commercially provide a polyurethane raw material having an easy handling.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing liquid diphenylmethane diisocyanate, which comprises adding a phospholine catalyst and a phosphorous acid ester of the formula (I):

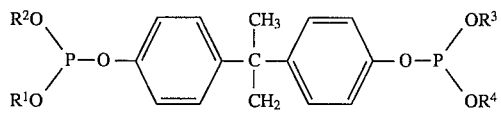

or the formula (II)

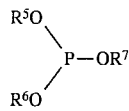

wherein $R^1$, $R^2$, $R^3$, $R^4$, $R^5$, $R^6$ and $R^7$ are the same or different, and each represents a $C_4$–$C_{20}$ alkyl group, to diphenylmethane diisocyanate, stirring the mixture at a temperature of from 60° to 80° C. for a period of from 1 to 10 hours, and adding a deactivating agent to the mixture once the desired degree of carbodiimidization has been reached.

* * * * *